United States Patent [19]

Bahrmann et al.

[11] Patent Number: 5,367,107
[45] Date of Patent: Nov. 22, 1994

[54] PROCESS FOR THE PREPARATION OF ALDEHYDES

[75] Inventors: Helmut Bahrmann, Hamminkeln; Peter Lappe, Dinslaken, both of Germany

[73] Assignee: Hoechst Aktiengesellschaft, Germany

[21] Appl. No.: 166,577

[22] Filed: Dec. 13, 1993

[30] Foreign Application Priority Data

Dec. 17, 1992 [DE] Germany ............................... 4242723

[51] Int. Cl.$^5$ .............................................. C07C 45/50
[52] U.S. Cl. ...................................... 568/454; 568/451
[58] Field of Search .................................. 568/454, 451

[56] References Cited

U.S. PATENT DOCUMENTS

| | | | |
|---|---|---|---|
| 526,942 | 3/1876 | Cawse | 260/449 R |
| 4,599,206 | 7/1986 | Billig et al. | 558/85 |
| 4,945,185 | 7/1990 | Papa et al. | 568/387 |
| 4,960,949 | 10/1990 | Devob et al. | 568/454 |

FOREIGN PATENT DOCUMENTS

| | | |
|---|---|---|
| 107430 | 5/1984 | European Pat. Off. . |
| 2489308 | 3/1982 | France . |
| 1692 | 8/1980 | WIPO . |

*Primary Examiner*—Werren B. Lone
*Attorney, Agent, or Firm*—Jordan B. Bierman

[57] ABSTRACT

The hydroformylation of olefins in liquid phase in the presence of an aqueous solution containing water-soluble rhodium-phosphine complex compounds as catalysts and salts of quaternary phosphonium compounds as solubilizers.

8 Claims, No Drawings

PROCESS FOR THE PREPARATION OF ALDEHYDES

This Application claims the benefit of the priority of German Application P 42 42 723.1, filed Dec. 17, 1992.

The invention relates to a process for the preparation of aldehydes by hydroformylation of olefins in the presence of water-soluble rhodium complex catalysts.

BACKGROUND OF THE INVENTION

In a variant of the oxo synthesis, which has been carried out on a large scale in industry for many years, the reaction of olefins with synthesis gas takes place in the presence of an aqueous solution of complex rhodium compounds as the catalyst. The principles of this process are described in DE-C-2 627 354, and its technical configuration is the subject of EP-B-103 810. A characteristic of this process is the use of rhodium compounds containing sulfonated triarylphosphines as complex ligands. Its advantages over the reaction using a homogeneous catalyst are based primarily on the formation of a very high proportion of unbranched aldehydes from n-olefins and the easy removal of the catalyst from the reaction product after the reaction has ended. This removal is performed simply by separating the aqueous phase from the organic phase, i.e. without distillation and thus without additional thermal process steps which lead to an impairment of the aldehyde yield. In addition to sulfonated triarylphosphines, the complex constituents of water-soluble rhodium complex compounds which are employed also include carboxylated triarylphosphines.

The two-phase process is outstandingly suitable for the hydroformylation of lower olefins, in particular ethylene and propylene. If higher olefins such as hexene, octene or decene are employed, the conversion is substantially reduced, so that synthesis on an industrial scale is no longer economic. This reduction in the conversion is caused by the decrease in solubility of higher olefins in water, since the reaction takes place in the aqueous phase.

One way of overcoming this disadvantage is the process disclosed in EP-B-157 316. In the hydroformylation of olefins having more than 6 carbon atoms in the presence of rhodium complex compounds containing trisulfonated triarylphosphines as the catalyst, the process consists of adding a quaternary ammonium salt to the aqueous catalyst solution as a solubilizer. The ammonium ion of the salt contains a straight or branched chain alkyl, ω-hydroxyalkyl, alkoxy, or a substituted or unsubstituted aryl radical, having in each case from 6 to 25 carbon atoms; and 3 identical or different straight or branched chain alkyl or ω-hydroxyalkyl radicals having 1 to 4 carbon atoms.

A modification of this process is the subject of EP-B-163 234. This patent teaches the reaction of $C_6$- to $C_{20}$-olefins with hydrogen and carbon monoxide in the presence of rhodium and a sulfonated arylphosphine whose cation is a quaternary ammonium ion. The ammonium ion contains one alkyl or aralkyl radical having 7 to 18 carbon atoms, and 3 straight or branched chain alkyl radicals having from 1 to 4 carbon atoms.

The processes described for the hydroformylation of higher olefins have proven very highly suitable in practice. However, the effectiveness of the quaternary ammonium salts used as the solubilizer over long periods of time leaves something to be desired, since they have only limited stability to hydrolysis and thermal stress. The consequence of this characteristic is that the aqueous catalyst solutions can be used for a shorter time than solutions containing no solubilizer.

SUMMARY OF THE INVENTION

The foregoing defects can be overcome by a process for the preparation of aldehydes by reaction of $C_6$- to $C_{20}$-olefins with carbon monoxide and hydrogen in the liquid phase in the presence of an aqueous solution containing water-soluble rhodium-phosphine complex compounds as catalysts and containing solubilizers, at temperatures of 20° to 150° C. and pressures of 0.1 to 20 MPa. A feature of this process is that the solubilizers are salts of quaternary phosphonium compounds.

Surprisingly, the hydroformylation of higher olefins in the presence of an aqueous solution of water-soluble rhodium-phosphine complex compounds as catalysts in the presence of quaternary phosphonium salts as solubilizers is successful over a prolonged period with a high conversion and selectivity. The phosphonium compounds evidently do not affect the catalyst system, so that its activity is maintained. In addition to this, the phosphonium compounds prove to be very stable under the conditions of the oxo synthesis with water-soluble catalysts.

DETAILED DESCRIPTION OF THE INVENTION

Quaternary phosphonium compounds are substances which are available on the market. They can be obtained on an industrial scale by, for example, alkylating tertiary phosphines with haloalkanes. A review of other methods for their preparation is given in Houben-Weyl, Methoden der Organischen Chemie [Methods of Organic Chemistry], volume E1 (1982), page 491 ff.

The phosphonium compounds preferably employed in the process according to the invention are those of the formula

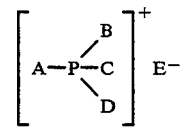

in which A is alkyl or aryl having in each case 6 to 18 carbon atoms or aralkyl having 7 to 18 carbon atoms; B, C, and D are straight- or branched chain alkyl radicals having 1 to 4 carbon atoms. E represents an anion and is halide, sulfate, tetrafluoroborate, acetate, methosulfate, benzenesulfonate, toluenesulfonate, lactate or citrate. Preferred anions are sulfate, methosulfate, sulfonate and lactate. The preparation of phosphonium salts with selected anions is expediently carried out by way of the quaternary phosphonium hydroxides. These are obtained, for example, from the halides which are passed in aqueous solution through a column of a strongly basic anion exchange resin. An appropriate process is described in, for example, DE-C-3 708 041. Examples of phosphonium compounds suitable for carrying out the process according to the invention are trimethyltetradecylphosphonium, tri-n-butylhexadecylphosphonium, tri-n-butylphenylphosphonium or tri-n-butylbenzylphosphonium salts. The concentration of the solubilizers in the aqueous catalyst solution is from 0.5 to 10% by weight, based on the catalyst solution.

The rhodium compounds employed as catalysts contain, bound as a complex, water-soluble phosphine, i.e. salts whose anion is a phosphine which contains at least one sulfonated or carboxylated aromatic radical. The term phosphine also includes those compounds of trivalent phosphorus in which the phosphorus atom is a component of a heterocyclic ring. The aromatic radical can be attached directly or via other groups to the phosphine phosphorus atom. Examples of aromatic radicals are the phenyl and the naphthyl radical. They may be sulfonated or carboxylated one or more times and may have further substituents, such as alkyl, hydroxyl, and halide.

Monophosphine anions are preferably derived from compounds of Formula

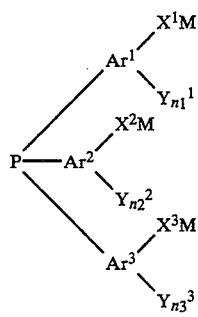

wherein $Ar^1$, $Ar^2$, and $Ar^3$ are each phenyl or naphthyl; $y^1$, $y^2$, and $Y^3$ are each straight or branched chain alkyl having 1 to 4 carbon atoms, alkoxy, halogen, OH, CN, $NO_2$, or $R^1R^2N$, wherein $R^1$ and $R^2$ are each straight or branched chain alkyl having 1 to 4 carbon atoms; $X^1$, $X^2$, and $X^3$ are each carboxylate ($COO^-$) or sulfonate ($SO_3^-$); and $n_1$, $n_2$, and $n_3$ are each an integer from 0 to 5. M is an alkali metal ion, a chemical equivalent of said alkaline earth metal, a zinc ion, or an ammonium or quaternary ammonium ion of the formula $N(R^3R^4R^5R^6)^+$ wherein $R^3$, $R^4$, $R^5$ and $R^6$ are each straight or branched chain alkyl having 1 to 4 carbon atoms. Particularly suitable compounds of Formula 1 are those in which $Ar^1$, $Ar^2$, and $Ar^3$ are each phenyl and $X^1$, $X^2$ and $X^3$ are each sulfonate.

Apart from the monophosphines, the anion may also comprise polyphosphines, in particular diphosphines, which contain at least one sulfonated or carboxylated aromatic radical. The diphosphine anions are preferably derived from diaryl compounds of Formula 2.

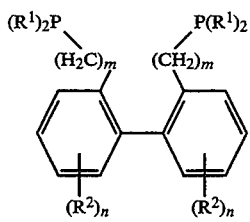

which are substituted by at least one sulfonate ($SO_3^-$) or carboxylate ($COO^-$) radical. In the formula, the $R^1$'s are each alkyl, cycloalkyl, phenyl, tolyl, or naphthyl; the $R^2$'s are each hydrogen, alkyl having 1 to 14 carbon atoms, alkoxy having from 1 to 14 carbon atoms, cycloalkyl having 6 to 14 carbon atoms, aryl having 6 to 14 carbon atoms, aryloxy having from 6 to 14 carbon atoms, or a fused-on benzene ring. The m's are each an integer from 0 to 5, and the n's are each an integer from 0 to 4. Proven representatives of this class of compounds are the products obtained by sulfonation of 2,2'-bis(diphenylphosphinomethyl)-1,1'-biphenyl or 2,2'-bis(diphenylphosphinomethyl)-1,1'-binaphthyl. One example of the anion of a heterocyclic phosphorus compound is 3,4-dimethyl-2,5,6-tris(p-sulfonatophenyl)-1-phosphanorbornadiene.

As the catalyst component, alkali metal salts—and in particular sodium salts—of the sulfonated or carboxylated phosphines are usually used. In accordance with a preferred embodiment of the invention, the phosphines are employed as phosphonium salts. The cation is in this case a phosphonium ion and corresponds to the cation of the solubilizer. This measure combines the catalytic properties of the phosphines with the solubilizing action of the phosphonium salts. In this variant of the process according to the invention, it is not necessary to employ all the phosphine as the phosphonium salt; rather it is sufficient to use only part of the complex ligand as the phosphonium salt while the remainder can be employed as the alkali metal salt.

The reaction of the olefins with hydrogen and carbon monoxide is carried out at temperatures of 20° to 150° C., in particular from 50° to 120° C., and at pressures of from 0.1 to 20 MPa.

The catalyst added to the reaction system may be preformed. However, with equal success, it can also be prepared from the components—the rhodium or rhodium compound and the aqueous solution of the sulfonated or carboxylated phosphine—under the conditions in the reaction mixture, i.e. in the presence of the olefin. In addition to metallic rhodium in finely divided form, the rhodium source may also comprise water-soluble rhodium salts, e.g. rhodium chloride, rhodium sulfate, or rhodium acetate, as well as compounds soluble in organic media such as rhodium 2-ethyl hexanoate, or insoluble compounds such as rhodium oxides.

The rhodium concentration in the aqueous catalyst solution is advantageously 10 to 2000 ppm by weight, based on the solution. The sulfonated or carboxylated phosphine is usefully employed in an amount such that there are 1 to 100 mol, preferably from 2 to 30 mol, of phosphine compounds per mol of rhodium. The pH of the aqueous catalyst solution should not be less than 2. The solution is generally adjusted to a pH of 2 to 13, preferably 4 to 10.

The ratio of carbon monoxide to hydrogen in the synthesis gas, can be varied within broad limits. The synthesis gas generally employed has a volume ratio of carbon monoxide to hydrogen of approximately 1:1. The reaction can be carried out either batchwise or continuously.

The process according to the invention is successfully employed in the hydroformylation of straight or branched chain olefins, irrespective of their molecular size. It is suitable with particular success for the reaction of olefins having six or more carbon atoms. The double bond in these olefins may be terminal or internal.

The following examples illustrate the invention without limiting it. The performance of the catalyst systems is characterized using, in addition to the ratio of n-aldehydes to i-aldehyde, the concepts of "activity" (A value), defined as $$\frac{\text{mol of aldehydes}}{\text{mol of } Rh \cdot \text{min}}$$

and "productivity" (P value), defined as $$\frac{\text{g of aldehydes}}{\text{cm}^3 \text{ of catalyst solution} \cdot h}.$$

The formation of alcohols and hydrocarbons is minimal.

EXAMPLE 1 a) Catalyst Preformation

A 1 liter autoclave with a dip pipe is charged with 569 ml of an aqueous solution comprising 212 g of trisodium tri(m-sulfophenyl)phosphine (0.12 mol), 382 g of water, and 200 ppm of Rh as rhodium acetate. Synthesis gas (volume ratio $CO/H_2$ 1:1) is injected to a pressure of 25 bar (2.5 MPa). The reaction solution is then treated for three hours at 110° C. with synthesis gas, while stirring, during which time the active catalyst is formed. After cooling to about 30° C., the stirrer is switched off and, after a settling time of 15 minutes, the excess solution (about 80 g) is removed via the dip pipe and analyzed. The remainder of the solution remains in the reactor.

b) Hydroformylation 250 g of tetradecene-1 is pumped with stirring into the solution prepared in accordance with a). At a constant pressure of 2.5 MPa, the mixture is heated to 110° C. and left at this temperature for 6 hours. It is then cooled to 70° C. and allowed to settle. The supernatant organic phase is removed via the dip pipe, weighed, and analyzed by gas chromatography. Substep b) is repeated twice. The results of these experiments (1.1, 1.2, and 1.3) are set forth in the Table. The conversion is only 0.1%. The values for activity and productivity relate to the amounts of aqueous inorganic phase present in the autoclave. The density of the aqueous phase is 1.055 g/cm³.

EXAMPLE 2 a) Catalyst Preformation

A 1 liter autoclave with a dip pipe is charged with 569 ml of an aqueous solution comprising 212 g of trisodium tri(m-sulfophenyl)phosphine (0.12 mol), 15.8 g of tetradecyltriethylphosphonium bromide, 30 g of buffer solution (pH 6.0), 336 g of water, and 200 ppm of Rh as rhodium acetate. Synthesis gas ($CO/H_2$=1:1) is injected to a pressure of 2.5 MPa. The reaction solution is then treated for three hours at 110° C. with synthesis gas, while stirring, during which time the active catalyst is formed. After cooling to about 30° C., the stirrer is switched off and, after a settling time of 15 minutes, the excess solution (about 80 g) is removed via the dip pipe and analyzed. The remainder of the solution remains in the autoclave.

b) Hydroformylation 250 g of tetradecene-1 is pumped with stirring into the solution prepared in accordance with a). At a constant pressure of 2.5 MPa, the mixture is heated to 110° C. and left at this temperature for 6 hours. It is then cooled to 70° C. and allowed to settle. The supernatant organic phase is removed via the dip pipe. It is weighed and analyzed by gas chromatography. Substep b) is repeated four times. The results of these experiments (2.1, 2.2, 2.3, 2.4, and 2.5) are set forth in the Table. The conversion increases sharply and stabilizes at a reduced level. The values for activity and productivity relate to the quantities of aqueous inorganic phase present in the autoclave. The density of the aqueous phase is 1.057 g/cm³.

EXAMPLE 3 a) Catalyst Preformation

A 1 liter autoclave with a dip pipe is charged with 569 ml of an aqueous solution comprising 212 g of trisodium tri(m-sulfophenyl)phosphine (0.12 mol), 20.4 g of tributylhexadecylphosphonium bromide, 30 g of buffer solution (pH 6.0), 332 g of water, and 200 ppm of Rh as rhodium acetate. Synthesis gas (volume ratio $CO/H_2$ 1:1) is injected to a pressure of 2.5 MPa. The reaction solution is then treated for 3 hours at 110° C. with synthesis gas, while stirring, during which time the active catalyst is formed. After cooling to about 30° C., the stirrer is switched off and, after a settling time of 15 minutes, the excess solution (about 80 g) is removed via the dip pipe and analyzed. The remainder of the solution remains in the autoclave.

b) Hydroformylation 250 g of tetradecene-1 is pumped with stirring into the solution prepared in accordance with a). At a constant pressure of 2.5 MPa, the mixture is heated to 110° C. and left at this temperature for 6 hours. It is then cooled to 70° C. and allowed to settle. The supernatant organic phase is removed via the dip pipe. It is weighed and analyzed by gas chromatography. Substep b) is repeated three times in all. The results of these experiments (3.1, 3.2, 3.3, and 3.4) are set forth in the Table. The conversion stabilizes at an increased level with respect to the blank experiment. The values for activity and productivity relate to the amounts of aqueous and organic phase remaining in the autoclave. The density of the aqueous phase is 1.059 g/cm³.

TABLE

|  | Example 1 | | | Example 2 | | | | | Example 3 | | | |
| --- | --- | --- | --- | --- | --- | --- | --- | --- | --- | --- | --- | --- |
|  | 1.1 | 1.2 | 1.3 | 2.1 | 2.2 | 2.3 | 2.4 | 2.5 | 3.1 | 3.2 | 3.3 | 3.4 |
| Conversion (by GC° m %) | 0.10 | 0.10 | 0.11 | 74.2 | 48.6 | 42.1 | 37.0 | 28.4 | 34.1 | 8.8 | 5.3 | 5.8 |
| A value | 0.00 | 0.00 | 0.00 | 3.10 | 1.66 | 1.32 | 1.13 | 1.01 | 1.17 | 0.21 | 0.11 | 0.11 |
| P value | 0.00 | 0.00 | 0.00 | 0.075 | 0.04 | 0.032 | 0.027 | 0.024 | 0.028 | 0.005 | 0.003 | 0.003 |

°gas chromatography

What we claim is:

1. A process for the preparation of aldehydes, at a temperature of 20° to 150° C. and under a pressure of 0.1 to 20 MPa, by reaction of olefins having 6 to 20 carbon atoms with carbon monoxide and hydrogen in a liquid phase in the presence of at least one solubilizer and a catalyst comprising an aqueous solution containing at least one water-soluble complex, said complex comprising a rhodium-containing component and a phosphine portion, said solubilizer comprising a salt of at least one quaternary phosphonium compound.

2. The process of claim 1 wherein said salt is of the formula

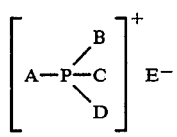

wherein A is alkyl having 6 to 18 carbon atoms or aryl having 6 to 18 carbon atoms, and B, C, and D are each straight or branched chain alkyl having 1 to 4 carbon atoms, and E is anion.

3. The process of claim 2 wherein said anion is selected from the group consisting of halide, sulfate, tetrafluoroborate, acetate, methosulfate, benzenesulfonate, toluenesulfonate, lactate, and citrate.

4. The process of claim 1 wherein said rhodium component contains, bound as a complex, trisulfonated and/or tricarboxylated triarylphosphines of the formula

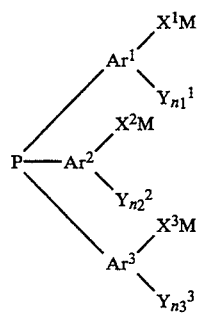 (1)

wherein $Ar^1$, $Ar^2$, and $Ar^3$ are each phenyl or naphthyl; $y^1$, $y^2$, and $y^3$ are each straight or branched chain alkyl having 1 to 4 carbon atoms, alkoxy, halogen, OH, CN, $NO_2$, or $R^1R^2N$, in which $R^1$ and $R^2$ are each straight or branched chain alkyl having 1 to 4 carbon atoms; $X^1$, $X^2$, and $X^3$ are each carboxylate (COO) or a sulfonate ($SO_3$); $n_1$, $n_2$, and $n_3$ are each an integer from 0 to 5, and M is alkali metal, alkaline earth metal, zinc, ammonium, or quaternary ammonium ion of the formula $N(R^3R^4R^5R^6)+$ wherein $R^3$, $R^4$, $R^5$, and $R^6$ are each straight or branched chain alkyl having from 1 to 4 carbon atoms.

5. The process of claim 4 wherein $Ar^1$, $Ar^2$, and $Ar^3$ are each phenyl and $X^1$, $X^2$, and $X^3$ are each sulfonate.

6. The process of claim 1 wherein the rhodium component contains, bound as a complex, diaryl compounds of the formula

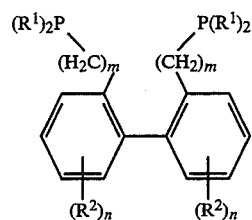

which are substituted by at least one sulfonate ($SO_3$) or carboxylate (COO), wherein the $R^1$'s are each alkyl, cycloalkyl, phenyl, tolyl, or naphthyl; the $R^2$'s are each hydrogen, alkyl having 1 to 14 carbon atoms, alkoxy having 1 to 14 carbon atoms, cycloalkyl having 6 to 14 carbon atoms, aryl having 6 to 14 carbon atoms, or aryloxy having 6 to 14 carbon atoms, or a fused-on benzene ring; the m's are each an integer from 0 to 5; and the n's are each an integer from 0 to 4.

7. The process of claim 2 wherein said anion is selected from the group consisting of sulfonated mono-, di-, and polyphosphines, carboxylated mono-, di-, and polyphosphines, and mixtures thereof.

8. The process of claim 1 wherein there is 0.5 to 10% by weight, based on the catalyst solution, of said solubilizer in said aqueous solution.

* * * * *